(12) United States Patent
Zhao

(10) Patent No.: US 6,476,203 B1
(45) Date of Patent: Nov. 5, 2002

(54) SAFE PHARMACEUTICAL COMPOSITION FOR TREATING AND PREVENTING INFERTILITY AND INCREASING IMMUNE FUNCTION

(76) Inventor: Xinxian Zhao, 67-08 168th St., Flushing, NY (US) 11365

( * ) Notice: Subject to any disclaimer, the term of this patent is extended or adjusted under 35 U.S.C. 154(b) by 0 days.

(21) Appl. No.: 10/096,971

(22) Filed: Mar. 14, 2002

(51) Int. Cl.[7] .................... A61K 31/70; A61K 39/385; A61K 31/35; A61K 35/78
(52) U.S. Cl. ........................ 536/8; 424/725; 514/25; 514/33; 514/456; 514/783
(58) Field of Search .................. 514/25, 456, 783, 514/33; 549/403; 536/8; 424/725

(56) References Cited

U.S. PATENT DOCUMENTS 6,399,579 B1 * 8/2000 Lenoble et al. ................. 536/8
6,123,944 A * 9/2000 Chen et al. .................... 514/456

* cited by examiner

Primary Examiner—Herbert J. Lilling

(57) ABSTRACT

The present invention relates to a new and safe pharmaceutical composition for treating and preventing infertilities and increasing immune function.

Specifically, this invention provides a new and safe composition, which is Icariin (ICN) extracted from *Epimedium sagittatum* Maxim, *E. brevicornum* Maxim and *E. macranthum* Morr. The chemical structure of Icariin is indicated. ICN also inhibits peroxidation significantly.

1 Claim, No Drawings

US 6,476,203 B1

SAFE PHARMACEUTICAL COMPOSITION FOR TREATING AND PREVENTING INFERTILITY AND INCREASING IMMUNE FUNCTION

BACKGROUND OF THE INVENTION

This invention relates to a new and safe pharmaceutical composition for treating of infertilities and increasing immune function.

Specifically, this invention provides a new and safe composition, which is Icariin extracted from *Epimedium sagittatum* Maxim, *E. brevicornum* Maxim and *E. macranthum* Morr. The chemical structure of Icariin is indicated.

DESCRIPTION OF THE PRIOR ART

The development of plant drug has progressed very successfully now. Taxol, for example, is a novel anticancer plant drug isolated from the needles and bark of the western yew, *Taxus brevifolia*. It is the prototype for a new class of anti-tumor drugs, which are characterized by their capacity to promote the assembly of microtubules. In tissue culture, taxol is a potent inhibitor of cell replication in the G or M phase of the cell cycle. Cytoplasmic microtubules in these drug-related cells are resistant to disassembly. In addition, these cells display an unusual inter-phase microtubule cytoskeleton consisting of free and bundled microtubules and lose their ability to migrate.

Clinical studies have demonstrated taxol to have antitumor activity indlude against advanced ovarian and breast cancer. Recent clinical trials have shown that paclitaxel and docetaxel may also be useful agents for the treatment of non-small-cell lung cancer, head and neck cancer, and other types of cancer.

The promising clinical activities of the anticancer taxol combined with potential problems due to limited supply generated a multitude of programs worldwide, such as broader clinical trials and in-depth clinical evaluation of anticancer taxol, efforts to provide an adequate supply of paclitaxel for clinical trials and for cancer patients, development of better drug formulations, biochemical studies to elucidate the precise mechanism of action, chemical studies to obtain structure activity information, development of second-generation paclitaxel analogues, elaboration of semisynthetic methods for the large scale production of the anticancer taxol, and efforts directed at the total synthesis of paclitaxel. Example of taxol indicated that pure natural medicine is very important. More important is in August 2000, FDA issued the draft version of "Guidance for Industry Botanical Drug Products ("Guidance"), which explains when a botanical drug may be marketed under an OTC drug monograph and when FDA approval of a NDA is required for marketing. It strongly shows the commitments of FDA to further open U.S. market to qualified botanical drugs. Many new regulatory approaches to access the safety and effectiveness of botanical drugs are recommended in the Guidance as follow, which differentiate botanical drugs from synthetic or highly purified drugs and hence remove some long-standing technical obstacles for the ultimate approval of FDA to admit qualified botanical drugs as new drugs in the U.S. The present invention relates to a new natural pharmaceutical composition comprising specific ingredients Icariin (ICN), which is extracted from *Epimedium sagittatum* Maxim, *E. brevicornum* Maxim and *E. macranthum* Morr. ICN, which is contrary to Taxol, does not have problems due to limited supply. The source of Morinda officinalis How is very plenty. In traditional Chinese medicine, it is mainly the dried root of *Epimedium sagittatum* Maxim, *E. brevicornum* Maxim and *E. macranthum* Morr. It has traditional used for treatment of impotence; cold pain of the lower abdomen; arthralgia due to wind, cold, beriberi, pain of loin and knee.

*Epimedium sagittatum* Maxim, *E. brevicornum* Maxim and *E. macranthum* Morr. are Chinese medical plants. However, according to traditional Chinese medical way, the whole plants or leaves, roots and fruit of plants were put into a bowl of water boiling nearby, then patients drank above liquid. This way, obviously, cannot be industrialize. In this invention, *Epimedium sagittatum* Maxim, *E. brevicornum* Maxim and *E. macranthum* Morr were extracted by plant biochemistry and obtained active ingredient. Further, the chemical structure of ingredient has been indicated.

So far, there are no any articles or patents reported that a safe pharmaceutical compound which is an extract of *Epimedium sagittatum* Maxim, *E. brevicornum* Maxim and *E. macranthum* Morr. were used for treating infertilities and increasing immune function.

DETAILED DESCRIPTION

The herbs named "*Epimedium sagittatum* Maxim, *E. brevicornum* Maxim and *E. macranthum* Morr.", has been recorded the treatment of sexual impotency by using alcohol extract of Morinda officinalis How and achyranthus L.

According to this invention, ICN is an efficient extract of possessing the effects of treating infertility and increasing immune function.

The sperm quality of the people has an obvious declining tendency in modern society. The average sperm volume ejaculated is 2.75 ml at present in comparison with 3.4 ml in 1940's. The average sperm concentration (density) has dropped from 113 to 66 million/ml. The average total amount of sperm ejaculated has been decreased by 53% in comparison with that in 1950's. In accordance with the report by Family Planning Technical Direction Station, male patients with infertility have occupied 21% among the whole male population. Up to now, there is no single effective drug of plant extract used for the treatment of male infertility.

The following examples are not intended, however, to limit or restrict the scope of the invention in any way, and should not be construed as providing conditions, parameters, reagents, or starting materials which must be utilized exclusively in order to practice the present invention.

EXAMPLE 1

Extraction of Icariin (ICN)

ICN extracted from plants named *Epimedium brevicornum* Maxim., *Epimedium sagittatum* Maxim., *Epimedium pubescens* Maxim., *Epimedium wushanense* T. S. Ying, and *Epimedium Koreanum* Nakai. The dried powder of plant was extracted with 95% of ethanol. Ethanol extraction was concentrated under reduced pressure and still residue obtained. The residue extracted by 95% of petroleum ether, $CH_2Cl_2$, acetic ether and n-butyl alcohol sequentially. N-butyl alcohol extraction was recovered and still residue obtained. The residue was passed through a column of polyamide and elute with ethanol. 10% of ethanol elute was passed through a column of silica gel and elute with $CHCl_3$—$CH_3OH$. Crystal was obtained from concentrated solution of $CHCl_3$—$CH_3OH$. Crystals were obtained after recrystalized from $CH_3OH$. The final product is Icariin.

Icariin has the following structure.

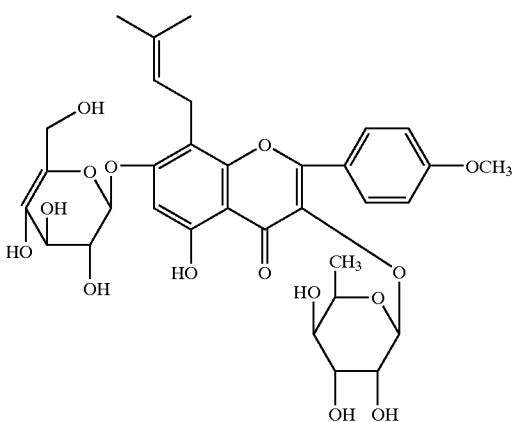

EXAMPLE 2
ICN Injecting Preparation

ICN, according to the conventional methods, was made as ampoules or other injection preparation, then sterilized. Type XGI S double door functional ampoule sterilizing machine is used for manufacturing of ICN injection. The function of facilities includes sterilization, leakage detection and washing. Microcomputer (PC machine) is applied in the principal controlling system. Dose is intramuscularly 5–100 mg daily.

EXAMPLE 3
ICN Oral Preparation

ICN powder granulated accorded to the conventional granulation method. The mixture content decreased from 100% to 93%. The 7% of content was different types of fillers. Disintegrants and lubricants were used: microcrystalline cellulose (Avicel PH 105, PH 101, PH 102, PH 200, all from FMC Corp., Lehmann and Voss and Co., Hamburg, Germany; and Vivacel 200, Rettenmaier and Söhne GmbH, Ellwangen-Holzmühle, Germany), microfine cellulose (Elcema P 050, P 100, G 250, all from Degussa A G, Frandfurt, Germany; and Tablettierhilfsmittel K, Merck KGaA, Darmstadt, Germany), lactose cellulose granulate (Cellactose, Meggle, Wasserburg, Germany), α-lactose monohydrate (Lactose D 80, Meggle, Wasserburg, Germany), and modified maize starch (Starch 1500, Colorcon GmbH, Königstein, Germany).

The disintegrants tested were the following: cross-linked sodium carboxymethyl cellulose (Ac-Di-Sol, FMC Corp./Lehmann and Voss and Co.; and Nymcel ZSB 10, Nymcel ZSB 16, METSÄ-SERLA, Njimegen, Netherlands), Cross-linked calcium carboxymethyl-cellulose (ECG 505, FMC Corp./Lehmann and Voss and Co.), potato starch (Caeleo, Hilden, Germany), sodium starch glycolate (Explotab, Gustav Parmentier, Frankfurt, Germany; and Primojel, AVEBE Deutschland, Düsseldorf, Germany), cross-linked polyvinylpyrrolidone (Kollidon C L, BASF A G, Ludwigsburg, Germany; and Polyplasdone XL, ISP Deutschland, Frechen, Germany), and low-substituted hydroxypropyl-cellulose (L-HPC LH 22, L-HPC LH 31, both from Shin-Etsu Chemical Co., Ltd., Tokyo, Japan).

For lubrication, the following were used: magnesium stearate (Otto Bärlocher GmbH, Munich, Germany), glyceryl tristearate (Dynasan 118, Hüls Ag, Witten, Germany), and polyethylene glycol (PEG 6000, Hoechst AG Frankfurt/Main, Germany).

Colloidal silicon dioxide (Cab-O-Sil M 5, Cabot GmbH, Hanau, Germany; Syloid 244, W. R. Grace and Co., Lexington, Ky., and Aerosil 200, Degussa A G, Frankfurt/Main, Germany) and hydrophobic colloidal silicon dioxide (Aerosil R 972, Degussa A G) were used. As a stabilizer, ascorbic acid (Merck KGaA, Darmstadt, Germany) was added.

The content of HUE was kept constant at a level of 100 mg per tablet. Tablet weight was varied between 100–105 mg. Tablet mixtures were mixed for 10 min in the Turbula mixer (type T2C, Willy Bachofen, Basel, Switzerland). The n lubricants were sieved through a 315-μm sieve into the mix. Final mixing was carried out for 5 min at 42 rpm in the Turbula mixer. The mixtures were compressed using a rotary press (Korsch PH 103, Korsch, Berlin). The lower compression roller was instrumented with four strain gauges (type 3/120 LY 11, Holtinger Baldwin, Inc., Darmstadt, Germany). A Philips carrier-frequency bridge (PR 9307 Philips, Kassel, Germany) was used for signal amplification. Each batch was compressed at different levels of compression force in the range of 1 to 25 kN. As a stabilizer, ascorbic acid (Merk KGaA, Darmstadt, Germany) was added. Sugar-coating operation was also performed conventionally.

The dosage of ICN is orally 50–200 mg daily.

EXAMPLE 4
Effect of ICN on Testosterone

Thirty normal Wistar male rats weighing 280+20 g were selected. Rats were divided 3 groups including normal group, control group and ICN group.

The rats were killed 30th days after the administration. The testosterone level of the rats in various groups was determined by using radioimmune method. The index of testis was determined. Control group was pathological model group. In control group, rats treated by cyclophosphamide (CYE). Rats treated by ICN+CYE in treatment group. The results are shown in Table 1.

TABLE 1

Effect of ICN on testosterone

| Group | Testosterone level (ng/dl X ± SD) |
| --- | --- |
| Normal (N) | 160.8 ± 20.2 |
| Control (C) | 78.9 ± 9.2 |
| Treatment (ICN) | 154.6 ± 19.8* |

*P < 0.001 compared with control group.

Data of Table 1 indicated that ICN could increase the level of testosterone significantly.

EXAMPLE 5
Effect of ICN On Seminal Vesicle and Living Sperms

Thirty normal male rats used in experiments. After killing rats, 100 mg of seminal vesicle was weighed, placed in nutrient solution of sperm and triturated then filtered and diluted. The number of sperms, and living sperms were counted by blood cell counting plate. The rate of living sperms was calculated. Temperature was kept at 20° C. when above proceeds. Stained by Gimesa-Wright method. 100 sperms were observed under oil immersion microscope and deformities of the sperm's heads, bodies and tails were examined. The results are shown in Table 2 and 3.

TABLE 2

Effect of ICN on seminal vesicle

| Group | Weight of seminal vesicle (mg/100 g body weight) |
| --- | --- |
| Normal (N) | 52.8 ± 6.7 |
| Control (C) | 30.4 ± 4.5 |
| Treatment (T) | 48.7 ± 5.8* |

*$P < 0.001$ compared with control group

TABLE 3

Effect of ICN on living sperms

| Group | % of living sperms |
| --- | --- |
| Normal (N) | 91.0 |
| Control (C) | 43.5 |
| Treatment T) | 85.8 |

EXAMPLE 6
Effect of ICN on Sexual Behavior

Selected 50 mice including male: 28–32g and female: 24–26g. The age of mice is over 8 weeks. The mice were divided normal group, suspend-loaded group, large dosage of ICN group, small dosage of ICN group and positive control group. The index of major sexual behaviors of male mice is ejaculation experiments operated on 15th day. The results are shown in Table 4.

TABLE 4

Effect of ICN on sexual behavior

| Group | Ejaculation proportion |
| --- | --- |
| Normal (N) | 100% |
| Control (C) | 62% |
| Treatment (T) | 93% |

The data of Table 4 indicated that ICN marked efficiency in treatment of infertility.

EXAMPLE 7
Effects of ICN on Hemopoietic System

Effects of ICN on hemopoietic system were investigated. Results showed that ICN could markedly improve the recovery rate of hemopoieses in treatment mice by cyclophosphamide. With increased cells in bone-marrow (BMC), endogenous colonies in spleen and higher $^3$H-TdR uptake in marrow and spleen. The level of serum colony stimulating factor (CSF) increased after injection. It was found that ICN protected the stem cells of bone marrow in mice from the killing effect of cyclophosphamide.

Pharmacological effects as illustrated by the following table: by means of the spleen colony assay technique the action of ICN on bone marrow stem cells (CFU-S).

TABLE 5

Effects of ICN on hemopoietic system

| Group | Number of sample | Mean (CFU-S ± SD) |
| --- | --- | --- |
| Normal (N) | 10 | 30.2 ± 3.0 |
| Control (C) | 10 | 6.8 ± 1.0 |
| Treatment (T) | 10 | 27.2 ± 3.0* |

*$P < 0.001$ compared with control group.

EXAMPLE 8
Effect of ICN on Phagocytosis of Peritoneal Macrophage of Mice

Experimental Procedure

Male mice weight 18–20 g were used in the experiments and were divided into treated (ICN) and control groups. The dosage of ICN was 5.5 mg/kg injected intraperitoneally. The control mice were injected with same volume of normal saline. These injections were repeated daily for 5 days, both treated and control group were injected intraperitoneally with cyclosphosphamide. The dosage of cyclophosphamide is 4.5 mg/kg.

The same experimental procedure for example 3, 4 and 5 in testing mice were used. Added 0.02 ml of 5% washed chick red blood cell suspension to 0.5 ml of the peritoneal exudates. Shook gently to mix and incubate at 37° C. for 5 minutes. Dipped two cover slips, closed to each other, in the above mixture and incubated for 30 minutes for the migration of the macrophages along the cover slips, fixed and stained with Sharma stain. Examined microscopically for:
Phagocytic rate—number of macrophages with phagocytized chick red blood cells per 100 macrophages counted.
Method of animal model is regular.

Results

TABLE 6

Effect of ICN on phagocytosis of peritoneal

| Group | Number of sample | Phagocytic (rate ± SD) |
| --- | --- | --- |
| Normal (N) | 10 | 33.3 ± 4.5 |
| Control (C) | 10 | 7.2 ± 0.9 |
| Treatment (T) | 10 | 28.5 ± 3.0* |

*$P < 0.01$ different from control group

EXAMPLE 9
Effect of ICN on White Blood Cells in Rats Treated by Cyclophosphamide Action of ICN and cyclophosphamide on white blood cells was investigated by means of white blood cells assay. It was revealed that ICN protected white blood cells in rats from the killing effect of cyclophosphamide. Method of testing in animal is standard. The dosage of ICN and cyclophosphamide is the same as in above examples. Time of treatment is 10 days. The results are listed below table:

TABLE 7

Effect of ICN on white blood cells

| Group | White blood cells × $10^3/cm^3$ ± SD | Number of sample |
| --- | --- | --- |
| Normal (N) | 14.8 ± 2.0 | 20 |
| Control (C) | 6.2 ± 7.0 | 20 |
| Treatment (T) | 12.8 ± 2.0* | 20 |

*$P < 0.01$ different from control group

EXAMPLE 10
Effect of ICN on Lymphoblastoid Transformation

By means of $^3$H-TdR liquid scintillation assay technique, the action of ICN on lymphoblastoid transformation was investigated method:
(1) Experimental procedure of animal is the same as in Example 2.
(2) Lemphoblastoid transformation test:
I. Reagents and conditions for cell culture
a. Culture media—RPMI 1640, medium 199 minimal essential medium (Eagle).
b. Buffer—Hepes buffer, the final concentration at 37° C. was 25 mM, to maintain the pH of the medium at 7.31.

c. Serum—generally 15–205 fetal bovine serum was incorporated, for lymphocytes from mice, 5% was used.
d. Gaseous phase—5% $CO_2$ in air.
e. Cell concentration—generally 1–2 c $10^6$/ml.
f. Stimulants—20μl/ml for phytohemagglutinin containing polysaccharide (PHA-M) or 10 μl/ml for polysaccharide-free purified phytohemagglutinin (PHA-P).

II. Measured by liquid scintillation
a. The conditions of cell culture are same as above. $^3$H-TdR was added after 48 hours of incubation at a final concentration of 1 μCi/ml and continued the incubation for 24 hours.
b. Washed the cells twice with cold normal saline and the erythrocytes were lysed. The intact lymphocytes were again washed once with cold saline. Spun down the lymphocytes and added 2 ml of 10% trichloroacetic acid to precipitate the protein. Washed twice with normal saline. Added 2 ml of ethanol:ether (1:1) to wash once. 0.2 ml of formic acid was then added for digestion till the precipitate was dissolved.
c. Added 4 ml of scintillation fluid to 0.1 ml of the final sample and counted in a liquid scintillation counter.

Results are listed in the following table:

TABLE 8

Effect of ICN on lymphoblastoid transformation

| Group | Number of sample | CPM ± SD |
|---|---|---|
| Normal (N) | 10 | 1480 ± 180 |
| Control (C) | 10 | 560 ± 85 |
| Treatment T) | 10 | 1150 ± 120* |

*P < 0.01 different from control group

EXAMPLE 11

Effect of ICN on Interleukin-2 (rIL-2)

The methods of determination rIL-2 were regular. The experimental data are listed in the following Table 9.

TABLE 9

Effect of ICN on interleukin-2 (rIL-2)

| Group | Number of sample | IL-2 (U/ml) ± SD |
|---|---|---|
| Normal (N) | 10 | 80.2 ± 8.8 |
| Control (C) | 10 | 51.0 ± 6.0 |
| Treatment (T) | 10 | 79.0 ± 8.5 |

EXAMPLE 12

Effects of ICN on Immune Function of Human Blood Lymphocytes

Twenty (20) old volunteers (60–70 years of age) and 10 healthy young persons participated in the experiment.

2 ml of venous blood, heparinized was obtained from each of the participants. The Study of the effects of ICN was carried out by using Eagle's Minimal Essential Medium MEM). MEM was supplemented with 0.125 ml of heat-inactivated fetal calf serum, 100 units of Penicillin and 0.1 mg of streptomycin per ml of medium. Culture medium was divided into treated (ICN) and control group. ICN was added to the culture medium of treatment group. The culture medium of control group was mixed with same volume as that of ICN of normal saline on the 72 hours of culture. The $^3$H-thymidine ($^3$H-TdR) was added into all the cultures (2 μci/ml) for last 12 hours of culture. The cells were harvested on 0.45 μm filters, washed with phosphate buffer (ph 7.4) and bleached with $H_2O_2$. The filters were then dried and the incorporation of $^3$H-TdR into lymphocytes cell was measured by scintillation counter.

TABLE 10

Effects of ICN on immune function of human blood lymphocytes

| | Young (n = 20) | | Old (n = 20) | |
|---|---|---|---|---|
| Index | Control | ICN | Control | ICN |
| CPM | 8200 ± 950 | 8155 ± 986 | 8750 ± 809 | 2500 ± 350 |
| P | <0.01 | | <0.01 | |

The data of Table 5–10 indicated that ICN could increase human immune function significantly.

EXAMPLE 13

Effect of SCS on Peroxidation

It is known that over lipid peroxidation caused a lot of diseases including cardiovascular disease and cancers. Therefore, inhibiting lipid peroxidation is very important.

The animal experiments were performed as previously described. Hepatic lipoperoxide content was determined.

In the present study, the effect of SCS on lipoperoxides was examined.

TABLE 11

Effect of ICN on peroxidation

| | Lipoperoxides (mmol MDA/g liver protein) | | | | |
|---|---|---|---|---|---|
| Group | 1 h | 3 h | 6 h | 12 h | 24 h |
| Control | 0.80 ± 0.09 | 0.90 ± 0.09 | 1.1 ± 1.0 | 1.3 ± 1.2 | 2.2 ± 2.0 |
| Treatment | 0.75 ± 0.08* | 0.70 ± 0.07** | 0.80 ± 0.9** | 0.70 ± 0.9** | 1.0 ± 0.12** |

*P < 0.05 compared with control group

It is known that the pathogenesis of $CCl_4$—induced hepatic damage involved reactive oxidant species increasing from the metabolism. The liver injure caused by $CCl_4$ is due to the formation of a reactive toxic metabolite by the hepatic cytochrome P-450 system. As data of Table 11 indicated that lipoperoxides are obviously increased in 1, 3, 6, 12 and 24 hours.

EXAMPLE 14
Pharmaceutical Preparations

Each dose for an adult is 50–300 mg. Using 50 kg as the average weight of an adult the dosage is 1–6 mg/kg. Therefore, it is very sage.

The preparation of pharmaceutical composition or drugs, which can be accomplished by the extraction methods set forth above or any conventional methods for extracting the active principles from the plants. The novelty of the present invention resides in the mixture of the active principles in the specified proportions to produce drugs, and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, capsules, tablets, syrups, elixirs, and solutions for parenteral injection with specified ranges of drugs concentration.

In addition, the present invention provides novel methods for treating and preventing a variety of cancer conditions and control cancer cells with produced safe pharmaceutical agent. It will thus be shown that there are provided compositions and methods which achieve the various objects of the invention and which are well adapted to meet the conditions of practical use. As various possible embodiments might be made of the above invention, and as various changes might be made in the embodiments set forth above, it is to be understood that all matters herein described are to be interpreted as illustrative and not in a limiting sense.

What is claimed as new and desired to be protected by Letter Patent is set forth in the appended claims:

1. A process for producing Icariin (ICN), which used for treating infertility and increasing immune function comprises:
   a. extracting said *Epimedium brevicornum* Maxim., *Epimedium sagittatum* Maxim; *Epimedium pubescens* Maxim., *Epimedium wushanense* T. S. Ying, and Epimedium Koreanum Nakai with 95% of ethanol;
   b. the ethanol extraction was recovered and the residue obtained;
   c. the residue extracted by 95% of petroleum ether, $CH_2Cl_2$, acetic ether and n-butyl alcohol sequentially;
   d. n-butyl alcohol extraction was recovered and residue obtained;
   e. the residue was passed through a column of polyamide and elute with ethanol;
   f. 10% of ethanol elute was passed through a column of silica gel and elute with $CHCl_3$—$CH_3OH_3$;
   g. the $CCl_3$—CH3OH solution concentrated under reduced pressure and the crystal was obtained; and
   h. the crystal was recrystalized from $CH_3OH$, and
   i. the final product was Icariin.

* * * * *